United States Patent [19]

Blaney et al.

[11] Patent Number: 4,795,452
[45] Date of Patent: Jan. 3, 1989

[54] ABSORBENT ARTICLE HAVING CANTILEVERED CUFF MEMBERS

[75] Inventors: Ted L. Blaney, West Chester; Mary E. Freeland, Norwood; Alvin D. Martin, Jr., Madeira, all of Ohio

[73] Assignee: The Procter & Gamble Company, Cincinnati, Ohio

[21] Appl. No.: 99,972

[22] Filed: Sep. 23, 1987

[51] Int. Cl.⁴ .............................................. A61F 13/16
[52] U.S. Cl. ............................................. 604/385.1
[58] Field of Search ............... 604/385.1, 385.2, 383, 604/380, 378

[56] References Cited

U.S. PATENT DOCUMENTS

| | | | |
|---|---|---|---|
| 3,766,922 | 10/1973 | Krusko | 604/380 |
| 3,860,003 | 1/1975 | Buell . | |
| 3,920,016 | 11/1975 | Mesek et al. | 604/378 |
| 3,976,074 | 8/1976 | Fitzgerald et al. | 604/378 |
| 4,014,341 | 3/1977 | Karami . | |
| 4,041,950 | 8/1977 | Jones, Sr. | 604/385.1 |
| 4,050,462 | 9/1977 | Woon et al. . | |
| 4,285,342 | 8/1981 | Mesek . | |
| 4,300,562 | 11/1981 | Pieniak . | |
| 4,486,192 | 12/1984 | Sigl . | |
| 4,490,148 | 12/1984 | Beckestrom . | |
| 4,578,071 | 3/1986 | Buell . | |
| 4,579,556 | 4/1986 | McFarland . | |
| 4,636,207 | 1/1987 | Buell | 604/385.2 |
| 4,643,728 | 2/1987 | Karami . | |
| 4,657,539 | 4/1987 | Hasse . | |
| 4,662,877 | 5/1987 | Williams . | |
| 4,681,579 | 7/1987 | Toussant et al. | 604/385.1 |
| 4,695,278 | 9/1987 | Lawson . | |
| 4,704,115 | 11/1987 | Buell . | |
| 4,704,116 | 11/1987 | Enloe . | |
| 4,738,677 | 4/1988 | Foreman | 604/385.1 |

FOREIGN PATENT DOCUMENTS 2159693 12/1985 United Kingdom .

Primary Examiner—C. Fred Rosembaum
Assistant Examiner—Mark O. Polutta
Attorney, Agent, or Firm—Steven W. Miller; John M. Pollaro; Fredrick H. Braun

[57] ABSTRACT

A disposable absorbent article such as a diaper having an outer covering layer comprising a liquid pervious topsheet and a liquid impervious backsheet, an absorbent core encased in the outer covering layer, and at least one cuff member extending outwardly from and along an edge of the absorbent core. The cuff member comprises an upper layer, a base layer, a cantilever flap interposed between the upper layer and the base layer and having a fixed edge and a distal edge, and gathering means such as a plurality of elastic members secured to the cantilever flap. The cuff member enhances containment and fit of the absorbent article and minimizes cuff roll-out and collapse during use.

20 Claims, 4 Drawing Sheets

ABSORBENT ARTICLE HAVING CANTILEVERED CUFF MEMBERS

FIELD OF THE INVENTION

The present invention relates to absorbent articles such as disposable diapers, and more particularly, to absorbent articles designed to have a contractible cuff member which improves containment of body exudates, conforms to the contours of the body of the wearer and permits movement of the body while maintaining contact with the body in motion.

BACKGROUND OF THE INVENTION

The major function of absorbent articles such as disposable diapers and adult incontinent briefs is to absorb and contain body exudates. Such articles are thus intended to prevent body exudates from soiling, wetting, or otherwise contaminating clothing or other articles such as bedding that come in contact with the wearer. A common mode of failure for such products occurs when body exudates leak out of the gaps between the article and the wearer's leg or waist to adjacent clothing before they have a change to be absorbed within the article. Another common mode of failure occurs when liquids wick out of a liquid soaked portion of the absorbent article along capillary channels.

Contemporary disposable diapers and absorbent pads such as those disclosed in U.S. Pat. No. 3,860,003 issued to Kenneth Barclay Buell on Jan. 14, 1975 entitled "Contractable Side Portions for Disposable Diaper"; U.S. Pat. No. 4,050,462 issued to Woon et al. on Sept. 27, 1977; and U.S. Pat. No. 4,579,556 issued to McFarland on Apr. 1, 1986; have a topsheet, a backsheet, an absorbent core, a flexible side flap and an elastic member associated with the side flap to gather the side flap to provide an elasticized leg flap along the longitudinal edges of the diaper. These elasticized leg flaps improve both wearing comfort and the ability of the diaper to contain body exudates by drawing the diaper snugly about the legs of the wearer, thereby forming a seal about the leg to prevent liquid from leaking out of the diaper.

Despite the effectiveness of such structures in containing exudates and providing good fit, body exudates can still leak from the edges of the diaper along the legs of the wearer to adjacent clothing and bedding. Because the side flaps are generally formed of portions of the topsheet and the backsheet that extend beyond the edges of the absorbent core, liquids will tend to flow by wicking through the side flaps to the longitudinal edges of the diaper where they can leak or wick to adjacent clothing or bedding because the side flap provides no barrier to the wicking of such liquids to the longitudinal edges.

Leakage of liquids along the legs of the wearer is further enhanced by the tendency of the elasticized flaps to invert or roll-out and collapse during use. Since the elastic member is secured directly to the backsheet and generally also the topsheet, the backsheet is pre-stressed such that the side flap generally bows or deflects above the surface of the absorbent core to form a boat-like shape along the longitudinal edges. While the side flap is pre-stressed upward during use, the leg of the wearer places forces on the side flap so that the elasticized flap will conform to the contours of the leg. These "in use" forces are opposite of the pre-stressed forces placed on the side flap such that if the "in use" forces exceed the forces "pre-stressed" in the backsheet, the side flap will tend to invert. Thus, the side flap will roll-out or not maintain complete contact with the leg of the wearer thereby allowing large gaps between the leg and the side flap that allows liquids to easily leak out of the edges of the diaper.

Therefore, it is an object of the present invention to provide an absorbent article which has improved containment characteristics.

It is an additional object of the present invention to provide an absorbent article having a cuff member which acts as a restraint against the leakage of body exudates.

It is a further object of the present invention to provide an absorbent article having a cuff member which reduces the potential for roll-out/collapse of a cuff member.

It is a still further object of the present invention to provide an absorbent article having a cuff member which reduces the potential of liquids to wick to the edges of the absorbent article thereby reducing the potential for liquids to wet the outer clothing of the wearer.

These and other objects of the invention will be more readily apparent when considered in reference to the following description and when taken in conjunction with the accompanying drawings.

SUMMARY OF THE INVENTION

In accordance with the present invention, a disposable absorbent article such as a diaper is provided with an outer covering layer comprising a liquid pervious topsheet and a liquid impervious backsheet, an absorbent core encased in the outer covering layer, and at least one cuff member extending outwardly from and along an edge of the absorbent core. The cuff member comprises an upper layer, a base layer underlaying the upper layer, an integral cantilever flap interposed between the upper layer and the base layer and having a fixed edge secured to the base layer and a distal edge disposed outboard of at least a portion of the edge of the absorbent core and having at least a portion free from securement to the underlying structure of the absorbent article, and gathering means such as a plurality of elastic members secured to the cantilever flap. In addition, closing means may secure the ends of the cantilever flaps to the underlying structure of the diaper so as to obviate inversion of the cantilever flaps during use.

The cuff member, and in particular the cantilever flap, enhances containment of liquids and other exudates by providing a liquid-impermeable seal along the edges of the absorbent article, a barrier wall that retards exudates from flowing along both the top surface of the topsheet and the multiple capillary channels such as formed between the topsheet and the backsheet or the topsheet and the skin of the wearer, and a gasketing action about the legs or waist of the wearer to maintain good fit during use, to reduce leakage, to maximize comfort for the wearer, and to minimize roll-out or inversion of the cuff member. The cantilevered cuff member has a reduced tendency to roll-out (invert) and collapse during use because of the way in which the cantilever flaps of the diaper or other absorbent article are pre-stressed and configured. The cuff member also provides the diaper with a bucket-like shape that provides better containment of liquids and other exudates because they are more readily retained within the structure of the diaper until absorbed and because more absorbent materials such as absorbent gelling materials, which tend to acquire exudates more slowly than conventional absorbent materials but which can retain much more exudates, may be positioned within the absorbent core to absorb and retain greater quantities of liquids.

In alternative embodiments of the present invention, the cuff member may additionally comprise a cantilever flap that is C-folded, a barrier member secured within the cuff member, and liquid migration resistant segments positioned on the upper layer of the cuff member. In addition, the absorbent article or diaper incorporating the present invention may be provided with a "T"-shaped absorbent core, an absorbent core that is scored to more reliably provide a deeper bucket-like shape, an umbilical notch, a pleated topsheet and/or an apertured film topsheet.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

Figure 1:
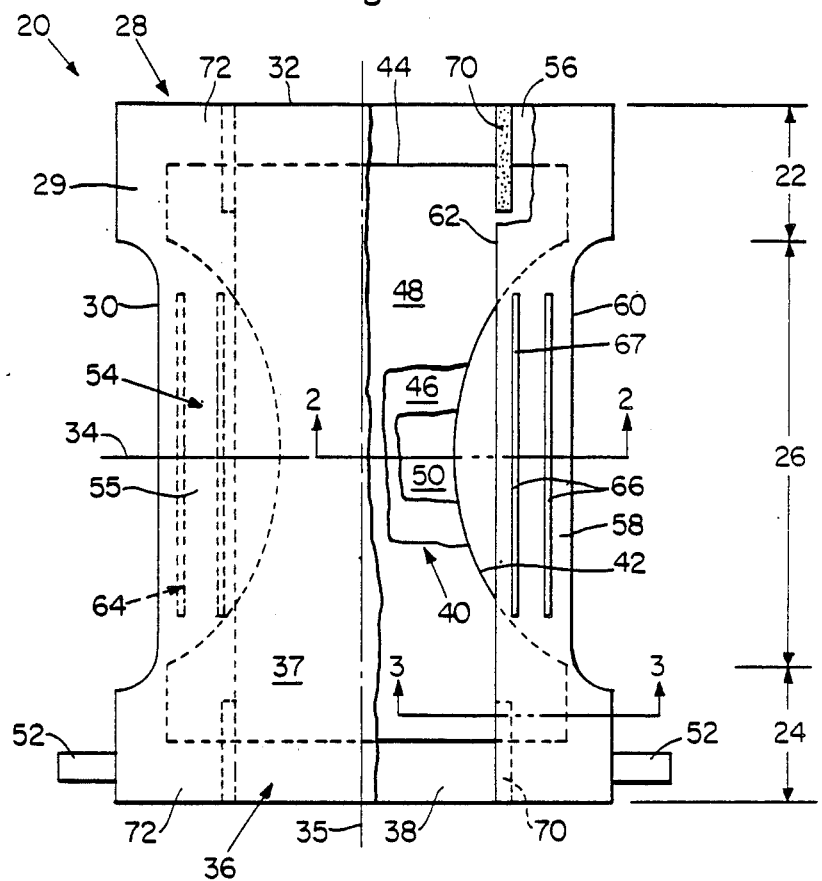
FIG. 1 is a plan view of a disposable diaper embodiment of the present invention having portions cut-away to reveal its underlying structure.
Figure 2:
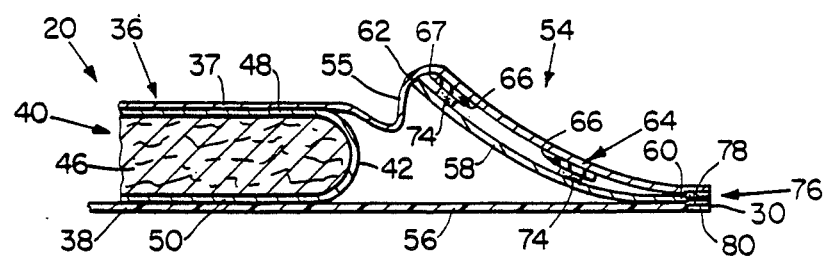
FIG. 2 is a fragmentary sectional view taken along section line 2—2 of FIG. 1.
Figure 3:
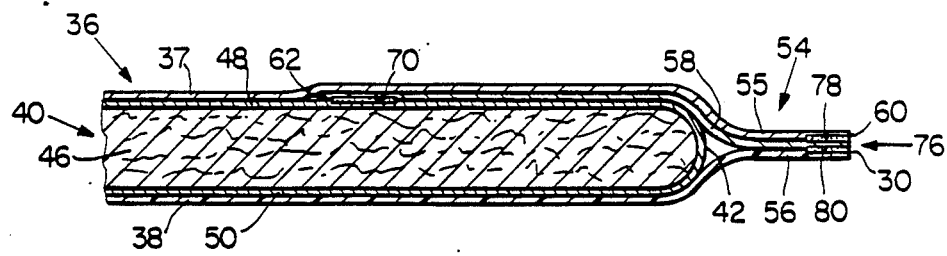
FIG. 3 is a fragmentary sectional view taken along section line 3—3 of FIG. 1.

As used herein, the term "disposable absorbent article" refers to articles which absorb and contain body exudates and more specifically refers to articles which are placed against or in proximity to the body of the wearer to absorb and contain the various exudates discharged from the body and which are intended to be discarded after a single use (i.e., they are not intended to be laundered or otherwise restored or reused). A preferred embodiment of the disposable absorbent article of the present invention, diaper 20, is shown in FIGS. 1-3. As used herein, the term "diaper" refers to a garment generally worn by infants and incontinent persons that is worn about the lower torso of the wearer. It should be understood, however, that the present invention is also applicable to other disposable absorbent articles such as incontinent undergarments, briefs, incontinent pads, sanitary napkins and the like.

FIG. 1 is a plan view of the diaper 20 of the present invention in its flat-out, uncontracted state (i.e., with all elastic induced contraction pulled out) with portions of the structure being cut-away to more clearly show the construction of the diaper 20 and with the portion of the diaper 20 which contacts the wearer facing the viewer. The diaper 20 is shown in FIG. 1 to have a front waist region 22, a back waist region 24, a crotch region 26, a perimeter 28 which is defined by the outer edges of the diaper in which the longitudinal edges are designated 30 and the end edges are designated 32, and a periphery 29. The diaper 20 additionally has a transverse centerline which is designated 34 and a longitudinal centerline which is designated 35.

The diaper 20 comprises an outer covering layer 36 preferably comprising a liquid pervious topsheet 37 and a liquid impervious backsheet 38; an absorbent core 40 having side edges 42 and waist edges 44, the absorbent core 40 preferably comprising an absorbent layer 46 and a first and second tissue layers 48 and 50, respectively; a pair of tape-tab fasteners 52; and an elastically contractible portion disposed along each longitudinal edge 30 (hereinafter referred to as a cuff member 54). Each cuff member 54 comprises an upper layer 55, a base layer 56, an integral cantilever flap 58 having a fixed edge 60 and a distal edge 62, and a gathering means 64 such as elastic members 66. The diaper 20 additionally comprises a closing means 70 for securing "closed" the end portions 72 of each cantilever flap 58 by securing at least a portion of the cantilever flap 58, preferably at least the distal edges 62 adjacent each end portion 72, to the underlying structure of the diaper 20 in the front and back waist regions 22 and 24.

FIG. 1 shows a preferred embodiment of the outer covering layer 36 which encases and contains the absorbent core 40 and preferably comprises the topsheet 37 and the backsheet 38 which are joined together in any suitable manner. As used herein, the term "joined" encompasses configurations wherein the topsheet 37 is directly joined to the backsheet 38 by affixing the topsheet 37 directly to the backsheet 38 and configurations wherein the topsheet 37 is indirectly joined to the backsheet 38 by affixing the topsheet 37 to an intermediate member, e.g. cantilever flap 58, that in turn is affixed to the backsheet 38. The topsheet 37 and the backsheet 38 preferably are coextensive and have length and width dimensions generally larger than those of the absorbent core 40 to thereby form the periphery 29 of the diaper 20. The periphery 29 thus comprises the portions of the diaper between the edges of the absorbent core 40 and the end edges 32 and the longitudinal edges 30.

The diaper 20 has front and back waist regions 22 and 24 respectively, extending from the end edges 32 of the diaper perimeter 28 toward the transverse centerline 34 of the diaper 20 a distance from about 1/5 to about ⅓ the length of the diaper 20. The waist regions comprise those portions of the diaper 20 which, when worn, encircle the waist of the wearer. The crotch region 26 is that portion of the diaper 20 between the front and back waist regions 22 and 24, and comprises that portion of the diaper 20 which, when worn, is positioned between the legs of the wearer and covers the lower torso of the wearer.

FIG. 2 is a fragmentary sectional view taken along line 2—2 of FIG. 1 and depicts a preferred diaper construction in the crotch region 26 of the diaper 20 as it is shaped before being applied to the wearer (i.e., the diaper is subjected to elastic contraction). The absorbent core 40 is shown to preferably comprise an absorbent layer 46 that is enveloped by a first and a second tissue layer 48 and 50. The absorbent core 40 is encased between the topsheet 37 and the backsheet 38; both the topsheet 37 and the backsheet 38 extending beyond the side edge 42 of the absorbent core 40 to define the longitudinal edge 30 of the diaper 20. A cuff member 54 extends outwardly from and along the side edge 42 of the absorbent core 40. The terms "outward" and "outboard" are defined as the direction away from the centerline of the diaper 20 that is parallel to the respective edge of the diaper 20 along which the cantilever flap 58 is disposed. ("Inward" and "inboard" defines the direction opposite of outward and outboard.) The cuff member 54 preferably comprises an upper layer 55 preferably formed by the portion of the topsheet 37 that extends beyond the side edge 42 of the absorbent core 40, a base layer 56 underlaying the upper layer 55 and that preferably is formed by the portion of the backsheet 38 which extends beyond the side edge 42 of the absorbent core 40, an integral cantilever flap 58 interposed between the upper layer 55 and the base layer 56 and having a fixed edge 60 and a distal edge 62, and a gathering means 64 such as the elastic members 66 operatively associated with the cantilever flap 58, preferably adjacent the distal edge 62, by preferably an elastic attachment means 74. The fixed edge 60 is secured to at least the base layer 56 and preferably both the upper layer 55 and the base layer 56 by a peripheral seam 76 to thereby form a liquid barrier seal along and adjacent to the longitudinal edge 30. Accordingly, the peripheral seam 76 comprises a first seam 78 which secures the upper layer 55, the topsheet 37, to the cantilever flap 58 and a second seam 80 which secures the cantilever flap 58 to the base layer 56, the backsheet 38. The distal edge 62 of the cantilever flap 58 is preferably disposed inboard of the fixed edge 60 to provide a cuff member 54 that is less likely to roll-out and collapse during use. The distal edge 62 is also preferably disposed outboard of the side edge 42 of the absorbent core 40 in at least the crotch region 26 so as to maximize both the fit of the cuff member 54 and the area of liquid acquisition of the absorbent core 40 in the crotch region 26. The innermost elastic member, i.e. the elastic member 66 positioned closest to the distal edge 62 that in this embodiment is elastic member 67, is spaced inwardly from the fixed edge 60 at least about ½ inch (about 12 mm), most preferably about ⅞ inch (about 21 mm), from the peripheral seam 76 that forms the fixed edge 60 so as to provide an effective shape for the diaper. As shown in FIG. 2, the distal edge 62 of the cantilever flap 58 is deflected upward away from the base layer 56 by the gathering action of the elastic members 66 to form a barrier wall that disrupts the capillary wicking channels in the crotch region 26, to draw and hold the cuff member 54 against the legs of the wearer, and to form a bucket-like or boat-like shape for the diaper 20.

FIG. 3 is a fragmentary sectional view taken along line 3—3 of FIG. 1 and depicts a preferred diaper construction in the back waist region 24 of the diaper 20. (Since the basic construction of the front waist region 22 will be generally the same as that of the back waist region 24, the basic construction of the diaper 20 in the back waist region 24 only will be described.) Because the waist regions must be both leakage resistant and comfortable for the wearer, the gathering means 64 preferably do not extend into the front and back waist regions 22 and 24 so that the cuff member 54 will lay flat against the waist of the wearer to thereby provide more comfort for the wearer while maintaining the containment characteristics of the diaper 20. Thus, as is shown in FIG. 3, the preferred construction of the cuff member 54 in the front and back waist regions 22 and 24 comprises the upper layer 55, preferably formed by the portion of the topsheet 37 that extends beyond the side edge 42 of the absorbent core 40, the base layer 56 that underlays the upper layer 55 and preferably is formed by the portion of the backsheet 38 which extends beyond the side edge 42 of the absorbent core 40, and the integral cantilever flap 58 secured to at least the base layer 56 and having a fixed edge 60 and a distal edge 62. The fixed edge 60 is preferably secured to the upper layer 55 and the base layer 56 by the peripheral seam 76 to thereby form a seal along the longitudinal edge 30. Accordingly, the peripheral seam 76 comprises a first seam 78 which secures the upper layer 55, topsheet 37, to the cantilever flap 58 and a second seam 80 which secures the cantilever flap 58 to the base layer 56, backsheet 38. The distal edge 62 is preferably disposed inboard of the fixed edge 60. The distal edge 62 preferably extends inboard beyond the side edge 42 of the absorbent core 40 in the waist regions of the diaper 20 due to the preferred hourglass configuration of the absorbent core 40 and the preferred rectangular configuration of the cantilever flap 58; however, the distal edge may alternatively be positioned outboard of the side edge 42 in the waist regions. As shown in FIG. 3, a closing means 70 preferably secures the distal edge 62 to the underlying structure of the diaper 20, either the absorbent core 40 and/or the backsheet 38, so as to provide a comfortable waist region and to obviate inversion of the cantilever flaps 58.

The backsheet 38 is impervious to liquids and is preferably manufactured from a thin flexible film, although other flexible liquid impervious materials may also be used. The backsheet 38 prevents the exudates absorbed and contained in the absorbent core 40 from wetting articles which contact the diaper such as bed sheets and undergarments. Preferably, the backsheet 38 is a polyethylene film having a thickness of from about 0.0012 mm (0.5 mil) to about 0.051 mm (2.0 mils), although other flexible liquid impervious materials may be used. As used herein, the term "flexible" refers to materials which are compliant and which will readily conform to the general shape and countours of the human body.

A suitable polyethylene film is manufactured by Monsanto Chemical Corporation and marketed in the trade as Film No. 8020. The backsheet 38 is preferably embossed and/or matte finished to provide a more clothlike appearance. Further, the backsheet 38 may be perforated or otherwise modified to permit vapors to escape from the absorbent core 40 while still preventing exudates from passing through the backsheet 38.

The size of the backsheet 38 is dictated by the size of the wearer and the exact diaper design selected. In a preferred embodiment, the backsheet 38 has a modified hourglass shape extending beyond the edges of the absorbent core 40 a minimum distance of at least about 1.3 cm to about 2.5 cm (about 0.5 to 1.0 inch) around the entire diaper perimeter 28. Thus, the portion of the backsheet 38 which extends beyond the side edges 42 of the absorbent core 40 in at least the crotch region 26 of the diaper 20 preferably forms the base layer 56 of the cantilevered cuff members 54.

The topsheet 37 is compliant, soft feeling, and non-irritating to the wearer's skin. Further, the topsheet 37 is liquid pervious, permitting liquids to readily penetrate through its thickness. A suitable topsheet may be manufactured from a wide range of materials such as porous foams, reticulated foams, apertured films, natural fibers (e.g., wood or cotton fibers), synthetic fibers (e.g., polyester or polypropylene fibers) or from a combination of natural and synthetic fibers. Preferably, the topsheet 37 is made of a hydrophobic material to isolate the wearer's skin from liquids in the absorbent core 40.

A particularly preferred topsheet 37 comprises staple length polypropylene fibers having a denier of about 1.5, such as a Hercules Type 151 polypropylene marketed by Hercules, Inc. of Wilmington, Del. As used herein, the term "staple length fibers" refers to those fibers having a length of at least about 15.9 mm (0.625 inches).

There are a number of manufacturing techniques which may used to manufacture the topsheet 37. For example, the topsheet 37 may be woven, nonwoven, spunbonded, carded, hydroformed or the like. A preferred topsheet 37 is carded and thermally bonded by means well known to those skilled in the fabrics art. Preferably, the topsheet 37 has a basis weight from about 15 to about 30 grams per square meter, a minimum wet tensile strength of at least about 400 grams per centimeter in the machine direction and a wet tensile strength of at least about 55 grams per centimeter in the cross-machine direction.

The topsheet 37 and the backsheet 38 preferably extend beyond the edges of the absorbent core 40 around the entire perimeter 28 and are joined together in the periphery 29. Preferably, a peripheral seam 76 (FIG. 2) placed anywhere in the periphery 29 is used to join the topsheet 37 to the backsheet 38. The peripheral seam 76 is preferably a continuous band of hot melt adhesive such as manufactured by Century Adhesives, Inc. of Columbus, Ohio and marketed under the tradename Century 5227. Alternatively, the peripheral seam 76 may be any suitable means as are known in the art such as ultrasonic sealing or heat/pressure sealing in any suitable configuration such as lines or closely spaced intermittent dots and dashes.

The peripheral seam 76 may be positioned at any convenient location on the diaper 20 considering the specific diaper configuration and the particular method used to manufacture the diaper 20. As shown in FIGS. 2 and 3, the peripheral seam 76 is preferably positioned outward from the absorbent core 40 in the periphery 29 of the diaper 20, preferably adjacent to the longitudinal edges 30 and the end edges 32, although it may alternatively be positioned anywhere in the periphery 29. Thus, the peripheral seam 76 preferably encircles the absorbent core 40, thereby encasing the absorbent core 40 between the topsheet 37 and the backsheet 38.

The absorbent core 40 may be any means which is generally compressible, conformable, non-irritating to the wearer's skin, and capable of absorbing and retaining liquids and certain body exudates. A preferred absorbent core 40 has first and second opposed faces and preferably comprises an absorbent layer 46 and first and second tissue layers 48 and 50, respectively. The first and second tissue layers 48 and 50 overlay the major surfaces of the absorbent layer 46 to form the first and second opposed faces of the absorbent core.

The absorbent layer 46 may be manufactured in a wide variety of sizes and shapes (e.g. rectangular, hourglass, asymmetric, etc.) and from a wide variety of liquid absorbent materials commonly used in disposable diapers and other absorbent articles, such as comminuted wood pulp which is generally referred to as airfelt. Examples of other suitable absorbent materials include creped cellulose wadding, absorbent foams, absorbent sponges, superabsorbent polymers, absorbent gelling materials, or any equivalent materials or combination of materials. The total absorbent capacity of the absorbent layer 46 should, however, be compatible with the design exudate loading in the intended use of the diaper. Further, the size and absorbent capacity of the absorbent layer 46 may be varied to accommodate wearers ranging from infants through adults. An example of a suitable absorbent layer 46 is discussed in U.S. Pat. No. 4,610,678 issued to Paul T. Weisman and Stephen A. Goldman on Sept. 9, 1986, and which patent is incorporated herein by reference.

A preferred embodiment of the diaper 20 shown in FIG. 1 has an hourglass-shaped absorbent layer 46 and is intended to be worn by infants ranging in weight from about 5 kilograms to about 12 kilograms (about 12 pounds to about 26 pounds). The airfelt used in the absorbent layer weights from about 10 grams to about 80 grams. It should be understood, however, that the size, shape, configuration, and total absorbent capacity of the absorbent layer 46 may be varied to accommodate wearers ranging from infants through adults. Therefore, the dimensions, shape, and configuration of the absorbent layer 46 may be varied (e.g., the absorbent layer 46 may have a varying caliper or hydrophilic gradient; or may contain absorbent gelling materials; or may be scored, preferably longitudinally along the length, so as to provide more flexibility for the core in certain regions so that the diaper may fold in a predictable manner to more easily assume a bucket shape and to provide wicking channels to spread liquids to the rest of the absorbent layer 46). The absorbent layer 46 is preferably about 25 cm wide (lateral dimension), about 47 cm long (longitudinal dimension) and approximately 7 cm across the narrowest part of the crotch region.

The first and second tissue layers 48 and 50 improve the tensile strength of the absorbent core 40 and reduce the tendency of the absorbent layer 46 to split, lump or ball when wetted. The first and second tissue layers 48 and 50 also help to improve lateral wicking of the absorbed exudates, thereby providing a more even distribution of the exudates throughout the absorbent layer 46. While a number of materials and manufacturing techniques may be used to manufacture the tissue layers, satisfactory results have been obtained with sheets of tissue paper having a basis weight of about 16 grams per square meter (10 pounds per 3,000 square feet) and having an air permeability of about 30.5 cubic meters per minute per square meter (100 cubic feet per minute per square foot) at a pressure differential of about 12.8 millimeters of water (½ inch). While the first and second tissue layers 48 and 50 are preferably coterminous with the absorbent layer 46, they may have different dimensions, different configurations, or they may be omitted entirely. (If the tissue layers are not coterminous with the absorbent layer 46 such that portions extend beyond the edges of the absorbent layer 46 to provide some absorbent material in the periphery 29, the edge of the absorbent core 40 would be defined by the edges of the absorbent layer 46 such as is described in the above-referenced U.S. Pat. No. 3,860,003 issued to K. B. Buell.)

The absorbent core 40 is superposed on the backsheet 38 and is preferably associated thereto by attachment means (not shown) such as those well known in the art, for example, pressure-sensitive adhesives, hot melt adhesives or other adhesives, ultrasonic bonding, or heat/pressure sealing. The absorbent core 40 may be secured to the backsheet 38 by a uniform continuous layer of adhesive, a patterned layer of adhesive, or an array of separate lines or spots of adhesive. An adhesive which has been found to be satisfactory is manufactured by Eastman Chemical Products of Kingsport, Tenn. and marketed under the tradename Eastobond A-3 or by Century Adhesives, Inc. of Columbus, Ohio and marketed under the tradename Century 5227.

Tape tab fasteners 52 are typically applied to the back waist region 24 of the diaper 20 to provide a fastening means to hold the diaper on the wearer. The tape tab fasteners 52 can be any of those well known in the art, such as the fastening tape disclosed in U.S. Pat. No. 3,848,594 issued to K. B. Buell on Nov. 19, 1974, which is incorporated herein by reference. These tape tab fasteners or other diaper fastening means, such as pins are typically applied near the end edges of a diaper in its "end-use" configuration.

A cuff member 54 extends outwardly from and along each portion of the edge of the absorbent core 40 from which it is desired to reduce liquid leakage by maintaining good fit about the waist or legs of the wearer. Thus, a cuff member 54 is disposed adjacent the perimeter 28 of the diaper 20, preferably adjacent each longitudinal edge 30 in at least the crotch region 26, so that the cuff member 54 tends to draw and hold the diaper 20 against the legs of wearer. Alternatively, a cuff member 54 may be disposed adjacent either or both of the end edges 32 of the diaper 20 to provide a waist cuff rather than leg cuffs. The cuff members 54 comprise an upper layer 55, a base layer 56, an integral cantilever flap 58 having a fixed edge 60 and a distal edge 62, and a gathering means 64 such as elastic members 66 secured to the cantilever flap 58.

The upper layer 55 is a flexible member that provides a comfortable layer between the gathering means 64 and the legs or waist of the wearer. The upper layer 55 may be manufactured from a wide variety of materials which are preferably compliant, soft feeling, and non-irritating to the wearer's skin since the upper layer 55 lays against the skin of the wearer. The upper layer 55 may be a woven or nonwoven material and may be manufactured from a wide range of materials such as porous foams, reticulated foams, apertured films, natural fibers (e.g., wood or cotton fibers), synthetic fibers (e.g., polyester or polypropylene fibers) or from a combination of natural and synthetic fibers. In general, any material which is suitable for use as the topsheet 37 is also suitable for use as the upper layer 55.

The base layer 56 underlays the upper layer 55 and is a flexible member that preferably forms the outer liquid impervious barrier along the longitudinal edges 30 of the diaper 20 beyond the side edges 42 of the absorbent core 40. The base layer 56 is thus that portion of the diaper 20 between the perimeter 28 and the edges of the absorbent core 40. The base layer 56 is preferably liquid impervious and is a polyethylene film, although other flexible, liquid impervious films may also be used. In general, materials which are suitable for use as the backsheet 38 are also suitable for use as the base layer 56. While the base layer 56 may comprise a separate element attached to the backsheet 38 adjacent the edges of the absorbent core 40, in a preferred embodiment of the present invention as shown in FIGS. 1-3, the base layer 56 is formed from the portion of the backsheet 38 extending from and along the side edges 42 of the absorbent core 40 in at least the crotch region 26.

A cantilever flap 58 is interposed between the upper layer 55 and the base layer 56 to enhance the containment of liquids along the edges of the diaper 20 by providing a liquid-impermeable seal along the edges, a barrier wall that retards exudates from flowing along both the top surface of the topsheet 37 and the capillary channels formed between the topsheet 37 and other diaper elements such as the backsheet 36 or between the topsheet 37 and the skin of the wearer, and a gasketing action about the legs or waist of the wearer to maintain good fit during use, to reduce leakage, to maximize comfort for the wearer, and to minimize roll-out of the cuff member 54. In a preferred embodiment as shown in FIGS. 1-3, a cantilever flap 58 is positioned adjacent each longitudinal edge 30 of the diaper 20 in at least the crotch region 26 to provide a cuff member 54 about each leg of the wearer. Of course, a multiplicity of cantilever flaps 58 or cuff members 54 may be positioned along various portions of the longitudinal edges 30 or the end edges 32 of the diaper 20.

While the cantilever flap 58 may be a formed using a number of manufacturing techniques, it is preferably formed by a separate element or strip of material which is positioned on and secured to the base layer 56. Alternatively, the cantilever flap 58 may be formed by any other means as are known in the art including folding the base layer 56, preferably the backsheet 38, onto itself, cutting out a portion of the folded over layers to form the narrow crotch region 26 of the diaper, and simultaneously or subsequently slitting the folded over edges along a portion of and alternatively along the entire longitudinal edge 30 to form a cantilever flap 58 which is a separate element from the base layer 56 in at least the crotch region 26. Thus, as used herein, the term "integral" cantilever flap designates a cantilever flap 58 that is a discrete separate element having its fixed edge 60 secured directly or indirectly to the base layer 56 and that is formed in a manner such as those described. The cantilever flap 58 is preferably formed by a separate strip of material that is positioned on and secured to at least the base layer 56 by the second seam 80 of the peripheral seam 76.

The cantilever flap 58 may be manufactured from a wide variety of materials such as polypropylene, polyethylene, polyester, rayon, nylon, foams, plastic films, apertured films and elastic foams. The cantilever flaps 58 are preferably hydrophobic and more preferably liquid impermeable so as to prevent the strikethrough of exudates. A particularly preferred cantilever flap 58 is manufactured from a thin, liquid impermeable material such as polyethylene or polypropylene film. The term "liquid impermeable" includes materials that retard the flow of liquid through the thickness of the material in at least one direction. Materials similar to those used for the liquid impervious backsheet 38 are generally suitable for use as the cantilever flap 58. In addition, the cantilever flaps 58 may be rendered liquid impermeable in any manner well known in the art such as selectively treating the cantilever flaps 58, untreating the cantilever flaps 58, or by securing a separate material to the cantilever flaps 58.

The cantilever flap 58 should also be flexible and thus elastically contractible so that when the gathering means 64 comprises one or a plurality of elastic members 66, the elastic members 66 may gather the cantilever flap 58 to provide a gasketing action about the legs or waist of the wearer and so that the distal edge 62 may be sufficiently deflected away from the base layer 56 so as to present a barrier wall against the lateral flow of body exudates. Thus, the cantilever flap 58 should also be made of a flexible material. "Flexible" is used herein to refer to materials which are compliant and which will readily conform to the general shape and contours of the human body.

As shown in FIGS. 1 and 2, each cantilever flap 58 has a fixed edge 60 and a distal edge 62. Thus, the cantilever flap 58 acts similar to a cantilever beam in that the distal edge 62 is deflected by forces acting upon the cantilever flap 58 due to the gathering action of the gathering means 64 so that the distal edge 62 will be deflected away from the base layer 56 to provide a barrier wall. The fixed edge 60 and the distal edge 62 are in spaced relation to each other and define the effective width of the cantilever flap 58. The fixed edges 60 and the distal edges 62 may be in a parallel, nonparallel, rectilinear or curvilinear relationship. In addition, the cantilever flap 58 may have a variety of different cross-sectional areas including circular, square, rectangular, or any other shape. Preferably, the fixed edge 60 is spaced from the distal edge 62 in a parallel and rectilinear relationship to provide a cantilever flap 58 having uniform width.

While the fixed edge 60 may be positioned anywhere between the perimeter 28 (longitudinal edge 30 or end edge 32) and the respective centerline of the diaper 20, the fixed edge 60 is preferably disposed between the outboard edge of the base layer 56, longitudinal edge 30, and the side edge 42 of the absorbent core 44 in at least the crotch region 26 so as to form a cap or seal against the leakage of liquid emanating from the edge of the absorbent core 40. As shown in FIG. 2, the fixed edge 60 is preferably secured to the base layer 56 adjacent the outboard edge of the base layer 56, longitudinal edge 30, to provide protection against leakage of liquid emanating from the edges of the absorbent core 40. In this preferred embodiment, the peripheral seam 76 secures the fixed edge 60 of the cantilever flap 58 directly to both the upper layer 55 and the base layer 56. Accordingly, the peripheral seam 76 comprises the first seam 78 which secures the topsheet 37 to the fixed edge 60 and a second seam 80 which secures the fixed edge 60 to the base layer 56.

The distal edge 62 may be disposed outboard or inboard of the fixed edge 60. For example, the distal edges 62 may be disposed outboard of the fixed edges 60 if the fixed edges 60 are secured to the base layer 56 adjacent the side edge 42 of the absorbent core 40. However, the distal edges 62 are preferably disposed inboard of the fixed edges 60 to provide a more effective cuff member 54. The distal edges 62 are maintained inboard of the fixed edges 60 by the closing means 70 and/or by being attached to the top layer 55 so as to obviate their inversion. In a particularly preferred embodiment, each distal edge 62 is disposed outboard from the side edge 42 of the absorbent core 40 in at least the crotch region 26 so as to provide a secure fit about the legs of the wearer and an effective gasketing action about the legs, and to maximize the liquid acquisition area above the absorbent core 40 in the crotch region 26.

The distal edge 62 is preferably free from securement to the base layer 56 in at least the crotch region 26 of the diaper 20 so that it may be spaced away or deflected from the base layer 56. The distal edge 42 is preferably spaced away from the base layer 58 so that the cuff member 54 presents a barrier wall against the lateral flow of body exudates and is biased so as to minimize cuff roll-out during use. As used herein, "spaced" includes embodiments wherein the distal edge 62 may assume one or more positions relative to the base layer 56 including at sometimes assuming a position adjacent to the base layer 56.

The gathering means 64 for gathering portions of the cantilever flap 58 is any member which gathers, contracts, stiffens, shortens or otherwise acts on the cantilever flap 58 so as to preferably deflect the distal edge 62 away from base layer 56 so as to cause the cantilever flap 58 to deflect or "cantilever" up to present a barrier wall against the lateral flow of body exudates and to provide a cuff member 54 that has a reduced potential to roll-out and collapse.

As shown in FIGS. 1 and 2, the gathering means 64 comprises one or preferably a plurality of elastic members 66 operatively associated with the cantilever flap 58 preferably adjacent the distal edge 62. Each elastic member 66 is preferably secured to the cantilever flap 58 in an elastically contractible condition so that in a normally unrestrained configuration, the elastic member 66 effectively contracts or gathers the cantilever flap 58. An elastic member 66 can be secured to the cantilever flap 58 in an elastically contractible condition in at least two ways as is discussed in U.S. Pat. No. 3,860,003 issued to Kenneth Barclay Buell which patent is incorporated herein by reference. In preferred embodiments of the present invention, the elastic members effectively contract the cantilever flap 58 about 15% to about 55%, more preferably about 30% to about 45%, and most preferably about 40%, at 10 grams to provide a cantilever flap that stands up during use and prevents red marking of the legs. The percent contraction is measured by the equation:

$$\text{Percent Contraction} = [(1 - L_{10}/L_m)] \times 100\%$$

wherein $L_m$ is the length of a segment of the elasticized flap measured while the flap is subjected to a tensile force sufficient to fully elongate the segment to its uncontracted state, typically this tensile force being about 210 grams, and $L_{10}$ is the length of the same segment measured while the flap is subjected to 10 grams of tensile force.

As shown in FIG. 2, each of the elastic members 66 is operatively associated with the cantilever flap 58 by securing it with an elastic attachment means 74 to the upper surface of the cantilever flap 58, although the elastic members 66 may alternatively be secured to the lower surface of the cantilever flap 58. The elastic members may also be additionally secured to the upper layer 55 by additional adhesive attachment means so as to further inhibit inversion of the cantilever flaps. While the elastic members 66 may be secured to the cantilever flap 58 adjacent only the ends of the elastic member 66, it is preferable to secure the entire length of the elastic member 66 to the cantilever flap 58. The elastic attachment means 74 herein are preferably glue beads made of hot melt adhesive such as manufactured by Findley Adhesives, Incorporated, Elm Grove, Wis., as Findley Adhesives 581. The elastic members 66 may also be affixed to the cantilever flap 58 in any of several other ways which are well known in the art. For example, the elastic members 66 may be ultrasonically bonded and/or heat/pressure sealed into the cantilever flap 58 using a variety of bonding patterns, or the elastic members 66 may simply be glued to the cantilever flap 58. A more detailed description of the manner in which the elastic members 66 may be positioned and secured to the cantilever flap 58 can be found in U.S. Pat. No. 4,081,301 issued to K. B. Buell, on Mar. 28, 1978, U.S. Pat. No. 3,860,003 issued to K. B. Buell on Jan. 14, 1975, and U.S. Pat. No. 4,253,461, issued to Strickland and Visscher on Mar. 3, 1981, all of which are incorporated herein by reference.

An elastic member 66 which has been found suitable for use in the cuff member 54 is an elastic strand having a cross section of 0.18 millimeters by 1.5 millimeters and made from natural rubber as available from East Hamptom Rubber Company of Stewart, Va., under the trademark E-1900 Rubber Compound. Other suitable elastic members can be made from natural rubber, such as the elastic tape sold under the trademark Fulflex 9211 by Fulflex Company of Scotland, N.C. The elastic member may also comprise any heat shrinkable elastic material as is well known in the art. Other suitable elastic members may comprise a wide variety of materials as are well known in the art including elastomeric films, polyurethane foams, elastomeric foams, and formed elastic scrim. In addition, the elastic members may take a multitude of configurations. For example, the width of the elastic members may be varied from about 0.25 mm (about 0.01 inches) to about 25 mm (about 1.0 inch) or more; the elastic members may comprise a single strand or a plurality of parallel or non-parallel strands of elastic material; or the elastic members may be rectilinear or curvilinear. In the embodiment illustrated in FIGS. 1 and 2, the gathering means preferably comprises a plurality of elastic members, each of the elastic members 66 extending along essentially the entire length of the cantilever flap 58 in the crotch region 26, although other lengths are cognizable.

The elastic members 66 to be effective should preferably be spaced inwardly from the fixed edge 60 of the cantilever flap 58 to establish an elasticized contractible line a distance from the fixed edge 60 and provide a cantilever flap width, i.e., the distance from the innermost elasticized contractible line to the fixed edge 60 which, in this embodiment, is from the lateral inboard edge of the innermost elastic member 67 to the inboard edge of the peripheral seam 76, second seam 80, measured when the diaper is in its flat-out uncontracted state. The spacing of the elastic members and the fixed edge 60 of the cantilever flap 58 provides more of a bucket-like shape for the diaper 20 that insures that the cantilever flap will stand-up during use. The innermost elastic member 67 should be spaced inwardly from the fixed edge 60 (have a cantilever flap width of) at least about ¼ inch (about 6 mm), more preferably at least about ½ inch (about 12 mm), and most preferably at least about 1 inch (about 25 mm).

The gathering means 64 may alternatively comprise several other elements as are known in the art. For example, stiffening means may disposed in or on each cantilever flap 58. The stiffening means must be sufficiently stiff so that the distal edge 62 is deflected away from the base layer 56. Suitable materials for the stiffening means include foams, nonwoven fabrics, batting, polyethylene film, formed films, spray glues, elastomeric foams, polyester, polyurethene or a high loft nonwoven material.

A preferred embodiment of the closing means 70 of the present invention for securing the end portions 72 of the cantilever flap 58 to the underlying structure of the diaper 20 are shown in FIGS. 1 and 3. The closing means 70 provide a more comfortable fit for the wearer and obviate inversion of the distal edges 62 of the cantilever flap 58 during application and use. Inversion is generally defined as the inboard disposed distal edge 62 turning outwardly when the diaper 20 is applied to the wearer. Thus, the closing means 70 may be any securement means positioned adjacent the end portions 72 of the cantilever flap 58 such that the end portions 72 may be directly or indirectly secured to the backsheet 38 or any of the other underlying structures of the diaper 20. In a preferred embodiment as shown in FIGS. 1 and 3, such closing means 70 are disposed in the front waist region 22 and the back waist region 24, and extend inboard of the waist edges 44 of the absorbent core 40 such that the end portions 72 are secured directly and indirectly to the backsheet 38 and directly to a portion of the absorbent core 40. The remaining portions of the distal edges 62 of the cantilever flaps 58 are not secured to any of the underlying structure of the diaper 20 so that the distal edges 62 are left freely deflectable to provide a cuff member 54 having improved containment that prevents roll-out and inversion during use. (The distal edges 62 may alternatively, however, be secured to the top layer 55 to further prevent inversion of the cantilever flaps 58). The closing means 70 are preferably adhesive beads consisting of hot melt adhesives such as marketed by Eastman Chemical Products, Company of Kingsport, Tennessee as Eastobond A-3 or by Findley Adhesives Incorporated, Elm Grove, Wis., as Findley Adhesives 581, although other closing means 70 such as ultrasonic bonding or heat/pressure sealing or any other securing means as are well known in the art may also be used.

The diaper 20 is applied to a wearer by positioning the back waist region 24 under the wearer's back and drawing the remainder of the diaper 20 between the wearer's leg so that the front waist region 22 is positioned across the front of the person. The ends of the tape-tab fasteners 52 are then secured preferably to outwardly facing areas of the diaper 20. In this manner, the cantilever cuffs 54 should be disposed in the crotch region of the wearer and should provide the dispositions and functions described hereinbefore.

While not wishing to be bound by any one theory describing the operation of the present invention, it is believed that an improvement in containment and fit is achieved in the following manner. As urine or other exudates are discharged onto the topsheet 37, some of the urine penetrates the topsheet 37 where it is absorbed by the absorbent core 40, some of the exudates flow on the surface of the topsheet 68, some of the exudates are absorbed by and wick laterally through the topsheet 37 and some of the exudates flow into the capillary channels formed at the interface between the topsheet 37 and the skin of the wearer.

The absorbed urine migrates throughout the absorbent core 40 moving from the point of discharge toward the edges of the absorbent core 40. Because the liquid impermeable integral cantilever flap 58 is secured to the liquid impermeable base layer 56 (backsheet 38) by the second seam 80 of the peripheral seam 76, the leakage-resistant seal or cap formed outboard of the side edge 42 of the absorbent core 40 retards the absorbed urine from leaking out of the perimeter 28 to minimize wetting of articles such as bedding or clothing that contact the edges of the diaper 20. The gap between the deflected cantilever flap 58 and the base layer 56 also disrupts the capillary channel formed in the periphery 29 such that liquids are less likely to wick to the edges of the diaper 20.

The surface exudates, likewise, move from the point of discharge toward the edges of the diaper 20 on the surface of the topsheet 38. As the surface material approaches the edges, the barrier wall formed by the spaced distal edges 62 of the cantilever flap 58 will be contacted. In normal use, the barrier wall will tend to block the flow of surface material, the material being held within the diaper 20 until absorbed or the diaper can be removed.

Liquid is retarded from wicking along the capillary channel formed between the topsheet 37 and the skin of the wearer by the elevational difference between the distal edge 62 of the cantilever flap 58 and the topsheet 37. Thus, liquid flowing between the wearer's skin and the topsheet 37 will encounter an area which is depressed below the wearer-contacting surface and is therefore not in contact with the wearer's skin. Thus, a discontinuity is created between the wearer's skin and the topsheet 37. This discontinuity interrupts the capillary channel and retards further liquid wicking toward the edges of the diaper.

Leakage prevention is further enhanced by the gasketing effect achieved by the cuff members 54, as they draw and gather the cantilever flaps 58 about the legs or waist of wearer, thereby providing an effective barrier against leakage. The cuff member 54 provides improved fit and containment because it is less likely to roll-out and collapse during use. The cuff member also provides a bucket-like shape for the diaper 20 when the gathering means 64 gather the cantilever flaps 58 such that free liquids are retained within the structure until absorbed by the absorbent core 40 and more absorbent material such as absorbent gelling materials may be placed within the absorbent core 40 to absorb and retain larger quantities of liquids though their fluid acquisition rate is slower than many fibrous absorbent materials.

It is believed that the cuff member 54 has a reduced tendency to roll-out (invert) and collapse because of the cantilever flap 58. In a conventional elasticized diaper, the absorbent core-facing surface of the backsheet is initially placed in compression due to the gathering forces of the elastic members. During use, however, this surface is placed in tension as the legs of the wearer bias the backsheet downwardly, the gathering action of the elastic members tending to want to pull the core-facing surface of the backsheet back into a compression mode, such that if the gathering forces of the elastic members are less than the forces of the legs on the backsheet, the cuff member will tend to invert and create gaps around the legs of the wearer.

The cantilever flap 58 reduces cuff inversion and collapse by putting the backsheet 38, the base layer 56, in a stable state prior to being applied to the wearer. The gathering action of the elastic member initially pre-stresses only the cantilever flap 58 to stand away from the base layer 56. Thus, when the diaper 20 is applied to the wearer, although forces applied by the leg of the wearer to the cuff member 54 tend to push the cuff member 54 to invert, the cantilever flap 58 biases the cuff member 54 such that the cuff member 54 will generally not invert and lose its sealing contact with the legs of the wearer.

In fact, it has also been found that the pre-stressing of the cantilever flap 58 can be used to advantage to provide an even more effective gasketing action about the wearer during use. If the cantilever flap 58 is pre-stressed to deflect or bow away from the base layer 56, i.e. the upper surface of the cantilever flap 58 is in compression, then in use, the cantilever flap will lie more securely against the leg of the wearer. The cantilever flap 58 will be biased further away from the base layer 56 during use such that the cantilever flap 58 will deflect into the leg of the wearer such that the cuff member 54 will tend to ride along the leg and conform to the shape of the leg much better to minimize gaps between the cuff member 54 and the leg thereby improving containment and fit.

Figure 4:
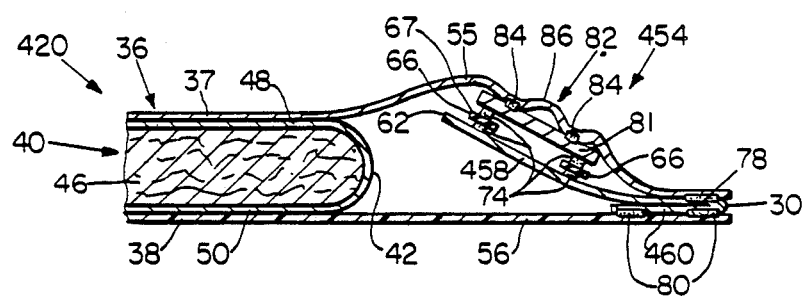
FIG. 4 is a fragmentary sectional view of an alternative embodiment of the present invention.

An alternative embodiment of the present invention is shown in FIG. 4. The cuff member 454 comprises a cantilever flap 458 that is C-folded such that the fixed edge 460 comprises an elongated segment of the cantilever flap 458. The cuff member 454 additionally comprises a barrier member 81 secured to the cuff member 454, preferably between the elastic members 66 and the upper layer 55, and liquid migration resistant segments 82 positioned on the upper layer 55. The barrier member 81 provides a vertically extending barrier wall that acts as a dam to the lateral flow of body exudates, particularly runny B.M., and as a soft member between the elastic members 66 and the skin of the wearer to thereby maximize comfort. The liquid migration resistant segments 82 provide improved liquid containment by redirecting the liquid away from the edges of the diaper 20.

As shown in FIG. 4, the cantilever flap 458 is preferably folded in a "C"-fold, although other folds such as "Z"-folds as are known in the art may be made in the cantilever flap 458. The fixed edge 460 of the "C"-folded cantilever flap 458 is formed from a segment of the cantilever flap 458 that is secured to the base layer 56 by the second seams 80, folded adjacent the longitudinal edge 30 of the diaper 420, and secured to the upper layer 55 by the first seam 78. The "C"-folded cantilever flap 458 provides enhanced containment of liquids because of the trough or pocket formed along the fixed edge 460 adjacent the longitudinal edge 30 by the folds. The liquid that migrates from the absorbent core 40 toward the edges of the diaper 420 are trapped by the trough within the diaper 20 such that containment may be enhanced. A "C"-folded cantilever flap 458 further minimizes roll-out and collapse of the cuff member 454. If the cantilever flap 458 is manufactured from a resilient material, the folded cantilever flap 458 will be further pre-stressed to deflect away from the base layer 56. Thus, the cantilever flap 458 will tend to conform to the shape of the leg to minimize gaps between the cuff member and the leg.

While a barrier member 81 can be positioned anywhere in the cuff member 454, the barrier member 81 is preferably positioned between the upper layer 55 and the elastic members 66 and secured to at least the elastic members 66 by elastic attachment means 74. The barrier member 81 can be made of any material that is sufficiently resilient with respect to the elastic members 66 so as to be longitudinally contractible thereby so that the cuff member 454 maintains sealing engagement with skin surfaces of the wearer during use. Examples of such resilient material are polyethylene, polypropylene, polyester, rayon, nylon, and polyurethane foam. Preferably, the barrier member 81 is made of a resilient material that recovers at least about 50%, more preferably at least about 70%, of its initial thickness at 5 minutes after being subjected to a pressure of 35.2 grams per square centimeter (0.5 pounds of square inch) for five minutes. The resilient material is preferably a substantially hydrophobic material having a basis weight of from about 30 to about 150, preferably from about 50 to about 100 grams per square meter. More preferably, it is a nonwoven web of thermoplastic material comprising polypropylene or polyester, particularly when such a web consists of inner bonded thermoplastic filaments having a denier of from about 6 to about 15.

Each barrier member 81 has thickness or caliper of at least about 1 millimeter, and preferably from about 2 millimeters to about 10 millimeters, so that the barrier wall has a height of at least about 1 millimeter, preferably from about 2 millimeters to about 10 millimeters, as measured when the diaper 420 is in its flat-out state with no load on the barrier member 81. The barrier member 81 generally has a width of from about 5 millimeters to about 40 millimeters, preferably from about 10 millimeters to about 30 millimeters, and a thickness ratio of from about 0.75 to about 8.0, preferably about 1.0 to about 6.0. The barrier member 81 can have varying shapes provided it presents a longitudinally extending, inboard facing barrier wall effective for damming lateral flow of body waste when included on the cantilever flaps 58. For example, the barrier member 81 may have a circular, square, trapezoidal, or rectangular cross-sectional area. Rectangular cross-sectional areas are preferred because they provide a vertical inboard facing barrier wall. More detail about the barrier members 81 is provided in U.S. Pat. No. 4,657,539 entitled "Waste Containment Garment Having Elasticized Barrier Wall Leg Flaps" issued on Apr. 14, 1987 to Margaret H. Hasse and which is incorporated herein by reference.

The liquid migration resistant segments 82 comprise a compacted portion 84 which alters the flow pattern of liquid as it moves from the point of discharge toward the edges of the diaper 20. The desired effect of the compacted portions 84 may be achieved in many ways such as by filling the inner voids of the compacted portions 84 with adhesive or other liquid impermeable material. In this manner, the compacted portion 84 is made to act as a barrier to the movement of liquid. In a preferred embodiment, however, the compacted portion 84 is compressed or densified relative to the other portions of the topsheet 37, which portions for convenience are designated uncompacted portions 86. The liquid migration resistant segments 82 are similar to those shown in U.S. Pat. No. 4,578,071 entitled "Disposable Absorbent Article Having An Improved Liquid Migration Perimeter Construction" issued to Kenneth B. Buell on Mar. 25, 1986 and U.S. Pat. No. 4,397,645 entitled "Disposable Absorbent Article Having An Improved Liquid Containment Construction" issued to Kenneth B. Buell on Aug. 9, 1983, both of which are incorporated herein by reference.

Figure 5:
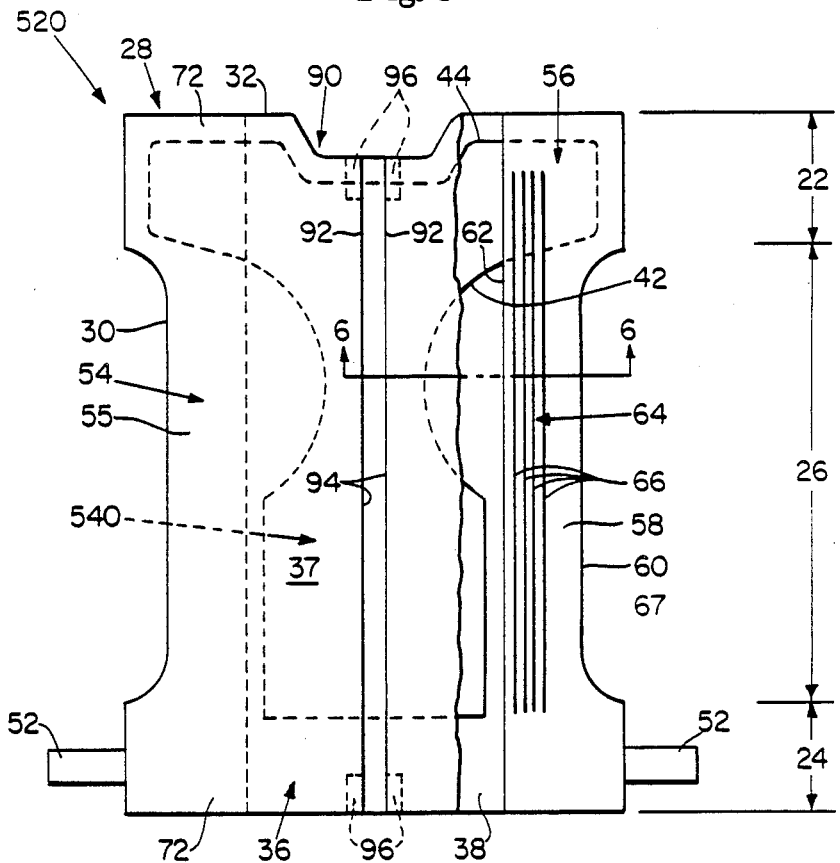
FIG. 5 is a plan view of a further alternative embodiment of the present invention having portions cut-away to reveal its underlying structure.
Figure 6:
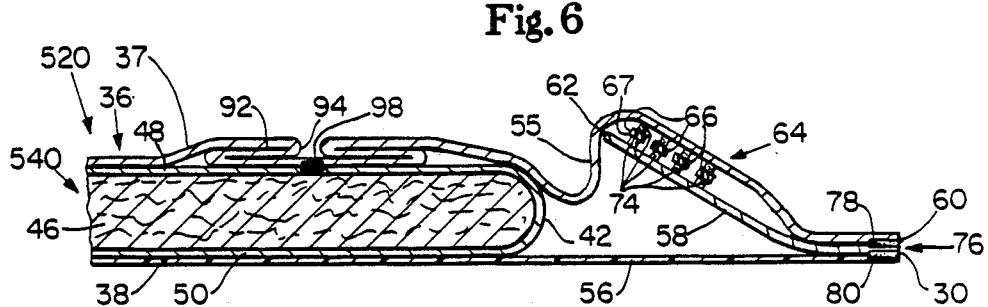
FIG. 6 is a fragmentary sectional view of the further alternative embodiment of the present invention of FIG. 5 taken along section line 6—6 of FIG. 5.

FIGS. 5 and 6 show a further alternative embodiment of the present invention, diaper 520. The diaper 520 is shown to additionally comprise an asymmetric, "T"-shaped absorbent core 540 encased in the outer covering layer 36, an umbilical notch 90 positioned in the front waist region 22 along the end edge 32, a pleated topsheet 37 having a pair of pleats 92 for improved liquid and solid containment, and a cuff member 54 having a gathering means 64 comprising four elastic members 66. The elastic members 66 are secured to both the cantilever flap 58 and the upper layer 55 (thus the upper layer is indirectly secured to the cantilever flap 58 at least adjacent the distal edge 62) by elastic attachment means 74 to further inhibit inversion of the cantilever flaps 58. The innermost elastic member 67 is spaced inwardly from the fixed edge 60 preferably at least about 1 inch (about 25 mm), most preferably about 17/16 inch (about 27 mm), to provide an effective cuff member 54 having a cantilever flap 58 that stands up during use. The diaper 520 shown in FIGS. 5 and 6 is especially useful for premature or very small infants, although other sizes up to those for adults is contemplated herein.

The absorbent core 540 has an asymmetric shape, preferably a "T"-shape, to provide more absorbency in the front of the diaper and to provide a more comfortable fit for the wearer. A "T"-shaped absorbent core 540 is preferred for economy and absorbency reasons because the core does not have ear regions disposed in the back half of the diaper. Less absorbent material is required to manufacture the absorbent core 540 so that the diaper 520 may be less expensive, and more of the absorbency of the core is placed in the front of the diaper where it is most needed. The asymmetric shape of the absorbent core 540 provides improved fit due to the configuration and placement of the core within the diaper. Examples of preferred "T"-shaped cores are disclosed in U.S. Pat. No. 3,860,003 issued to K. B. Buell on Jan. 14, 1975 and U.S. Pat. No. 4,336,806 issued to Repke on June 29, 1982.

Because newborn and premature infants are especially prone to infection and irritation of the umbilical cord, the diaper 520 is provided with an umbilical notch 90 to remove any covering of the umbilical cord which could cause irritation or soreness of the cord and which increases the opportunity for the cord to dry so as to reduce the likelihood of bacterial infection. The umbilical notch 90 is positioned, preferably centrally, along the end edge 32 of the perimeter 28 in the front waist portion 22 of the diaper 520. While the umbilical notch 90 may be V-shaped or U-shaped as is shown in U.S. Pat. No. 4,230,113 issued to Mehta on Oct. 28, 1960 or any other shape as known in the art, the umbilical notch is preferably a modified trapezoidal shape such as shown in FIG. 5. While the size of the notch is dependant upon the exact size of the diaper, the umbilical notch 90 is preferably about 3.5 cm wide at the base, about 9.0 cm wide at the end edge 32 and about 2.5 cm deep.

The topsheet 37 of the diaper 520 is preferably pleated so as to form a pair of pleats 92 that extend along the central portion of the absorbent core 540 in the longitudinal direction. The opposed pair of pleats 92 form channels in the central region of the diaper to acquire, contain, and hold body exudates until the exudates are absorbed by the absorbent core 540 or the diaper 520 is removed from the wearer. The pleats 92 also provide extra material in the topsheet 37 to allow the cantilever flaps 68 to freely stand up to form a bucket-like shape while limiting the amount of inversion of the flaps. The pleats 92 are preferably formed from folding the topsheet 37 at two separate locations such that the distal edges 94 of the pleats 92 are disposed adjacent each other. The topsheet folds are then secured together adjacent the end edges 32 of the diaper 520 by attachment means 96 as are known in the art to retain the shape of the pleats 92 during use and to allow the central portion of the pleats 92 to be freely moveable so that they may adjust their size and shape to fit the contours of the wearer. Additionally, the topsheet 37 is preferably secured to the absorbent core 540 along a narrow line between the pleats 92 by attachment means 98 to further prevent the cuff members 64 from inverting during use. The topsheet 37 also may preferably be tacked to the pleats 92 along a narrow section, preferably about four inches (100 mm) from the front edge of the umbilical notch (about five inches (125 mm) from the end edge 32), to more effectively allow the pleats to function.

Figure 7:
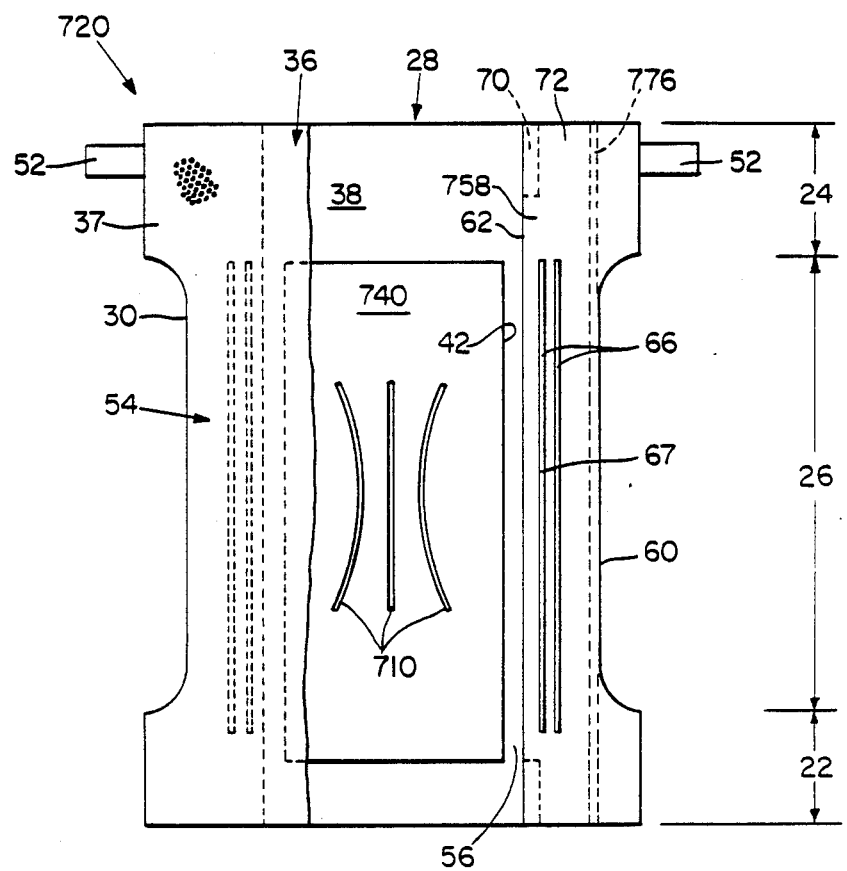
FIG. 7 is a plan view of a still further alternative embodiment of the present invention having portions cut-away to reveal its underlying structure.

FIG. 7 shows a further alternative embodiment of the present invention, diaper 720. The diaper has an hourglass-shaped outer layer 36 and a rectangular absorbent core 740. As shown in FIG. 7, the absorbent core 740 is scored along three lines 710 so that the absorbent core 740 will bend predictably to form a deeper bucket-like shape when the elastic members 66 gather the cantilever flaps 758. Since the diaper 720 can assume a much deeper bucket-shape, higher percentages of absorbent gelling materials can be incorporated into the absorbent core 740. The topsheet 37 preferably comprises an apertured film topsheet that is manufactured by the technique of hydroforming such as the film described in U.S. Pat. No. 4,629,643 entitled "Microapertured Polymeric Web Exhibiting Soft and Silky Tactile Impression" issued to John J. Curro and E. Kelly Linman on Dec. 16, 1986. The cantilever flaps 758 are preferably formed by folding the backsheet 38 onto itself, cutting and slitting the folded-over edges in the crotch region 26 to form the hourglass shape, and securing the fixed edges 60 of the cantilever flaps 758 to the base layer 56 by a peripheral seam 776 of a hot-melt adhesive to form an integral cantilever flap 758. The distal edge 62 of the cantilever flap 758 is disposed outboard from the side edge 42 of the absorbent core 740 along the entire length of the diaper 720 and the innermost elastic member 67 is spaced from the fixed edge 60 preferably at least about ½ inch (about 12 mm), most preferably about ¾ inch (about 18 mm), to form an effective bucket-shape for improved containment of exudates.

While particular embodiments of the present invention have been illustrated and described, it will be obvious to those skilled in the art that there are other changes and modifications that can be made without departing from the spirit and scope of the invention. It is therefore intended to cover in the appended claims all such changes and modifications that are within the scope of this invention.

What is claimed is:

1. A disposable absorbent article having a front waist region, a back waist region and a crotch region, said absorbent article comprising:
    an outer covering layer;
    an absorbent core having side edges that is encased in said outer covering layer;
    a cuff member extending outwardly from and along each side edge of said absorbent core in at least the crotch region, each of said cuff members comprising
    (i) an upper layer,
    (ii) a base layer underlaying said upper layer,
    (iii) an integral cantilever flap interposed between said upper layer and said base layer, said cantilever flap having a fixed edge and a distal edge, said fixed edge being secured to at least said base layer adjacent the longitudinal edge of the absorbent article, said distal edge being disposed inboard of said fixed edge and outboard of said side edges of said absorbent core in at least the crotch region and having at least a portion free from securement to the base layer in at least the crotch region, and
    (iv) gathering means operatively associated with said cantilever flap for gathering said cantilever flap so that said distal edge is deflected away from said base layer.

2. The absorbent article of claim 1 wherein said cantilever flap is liquid impermeable.

3. The absorbent article of claim 2 wherein said base layer is liquid impermeable.

4. The absorbent article of claim 3 wherein said upper layer is liquid permeable.

5. The absorbent article of claim 4 additionally comprising a peripheral seam for securing said base layer and said cantilever flap together so as to provide a liquid impermeable seal along the edges of said absorbent article.

6. The absorbent article of claim 5 wherein said outer covering layer comprises a liquid pervious topsheet and a liquid impervious backsheet, said backsheet extending beyond the side edges of said absorbent core to define said base layer and said topsheet extending beyond the side edges of said absorbent core to define said upper layer.

7. The absorbent articles of claim 6 additionally comprising closing means for securing the distal edges of said cantilever flaps to the underlying structure of the absorbent article in the front and back waist regions.

8. The absorbent article of claim 7 wherein said gathering means comprises an elastic member spaced inwardly from said fixed edge at least about ¼ inch.

9. The absorbent article of claim 7 wherein said gathering means comprises a plurality of elastic members.

10. The absorbent article of claim 9 wherein the innermost of said elastic members is spaced inwardly from said fixed edge of at least about ¼ inch.

11. The absorbent article of claim 10 wherein said cantilever flap is secured to said top layer adjacent said distal edge so as to inhibit inversion of said cuff members.

12. The absorbent article of claim 9 additionally comprising a barrier member secured within said cuff member between said upper layer and said elastic members.

13. The absorbent article of claim 12 additionally comprising leakage resistant members positioned on said upper layer.

14. The absorbent article of claim 13 wherein said topsheet is pleated adjacent to the longitudinal centerline of the absorbent article.

15. The absorbent article of claim 14 additionally comprising an umbilical notch.

16. The absorbent article of claim 15 wherein said absorbent core has an asymmetrical shape.

17. The absorbent article of claim 9 wherein said elastic members are secured to said top layer so as to inhibit inversion of said cuff members.

18. The absorbent article of claim 17 wherein said absorbent core has a rectangular shape.

19. The absorbent article of claim 18 wherein said absorbent core is scored so as to predictably fold said absorbent core to provide a deeper bucket-like shape for the absorbent article.

20. The absorbent article of claim 19 wherein said topsheet comprises an apertured film.

* * * * *